United States Patent [19]
Schwab

[11] Patent Number: 5,233,409
[45] Date of Patent: Aug. 3, 1993

[54] COLOR ANALYSIS OF ORGANIC CONSTITUENTS IN SEDIMENTARY ROCKS FOR THERMAL MATURITY

[76] Inventor: Karl W. Schwab, 1718 Triway, Houston, Tex. 77043

[21] Appl. No.: 841,063
[22] Filed: Feb. 25, 1992
[51] Int. Cl.⁵ .................................. G01J 3/50
[52] U.S. Cl. .................................. 356/402; 356/406
[58] Field of Search .............. 356/402, 405, 406, 407; 364/498, 526

[56] References Cited

U.S. PATENT DOCUMENTS

| | | | |
|---|---|---|---|
| 4,043,675 | 8/1977 | Guennel et al. | 356/421 |
| 4,971,437 | 11/1990 | van Gijzel | 356/73 |
| 5,155,546 | 10/1992 | Balsam et al. | 356/300 |

Primary Examiner—F. L. Evans
Attorney, Agent, or Firm—Bush, Moseley & Riddle

[57] ABSTRACT

In accordance with an illustrative embodiment of the present invention, the state of the thermal maturity of organic matter extracted from a sedimentary rock sample is determined by using a microscope in combination with a color video camera to provide an image of the organic matter in transmitted and filtered light, using the output of the camera to compute RGB and HSB values for a selected area of the image on a per-pixel basis, and plotting values integrated over the selected area in the form of a thermal maturation pathway from which a likelihood that oil has been generated in the rock can be determined.

8 Claims, 3 Drawing Sheets

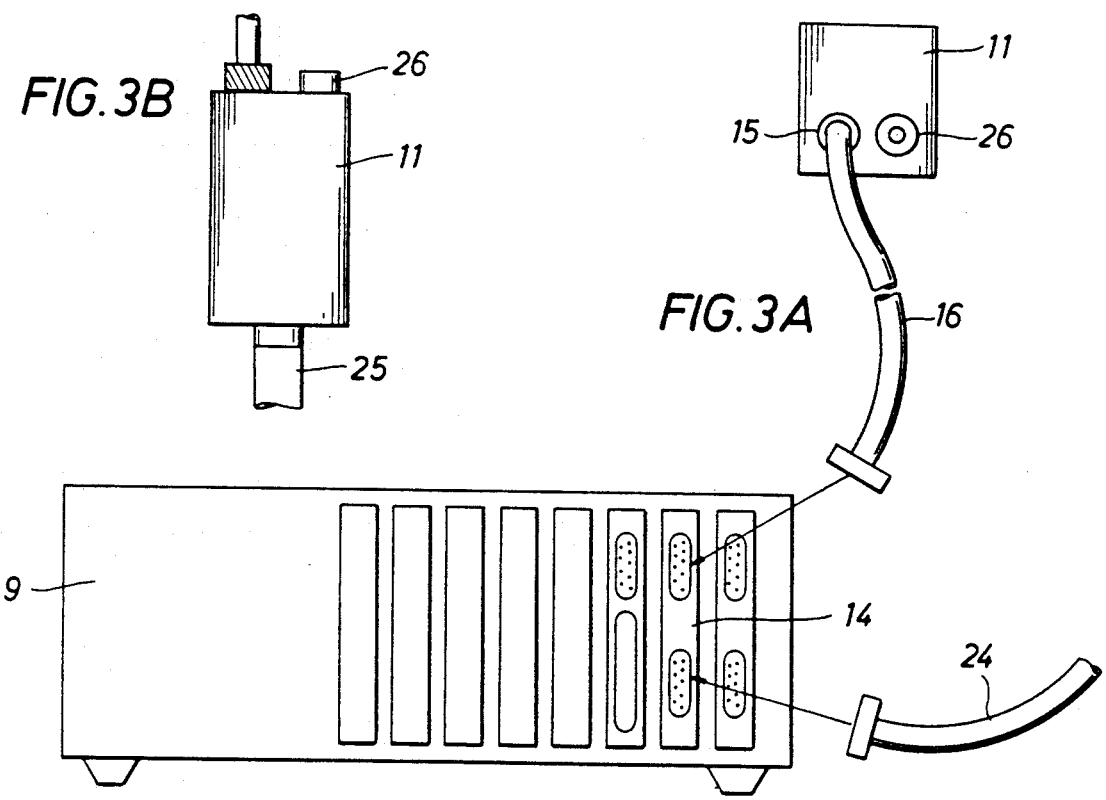
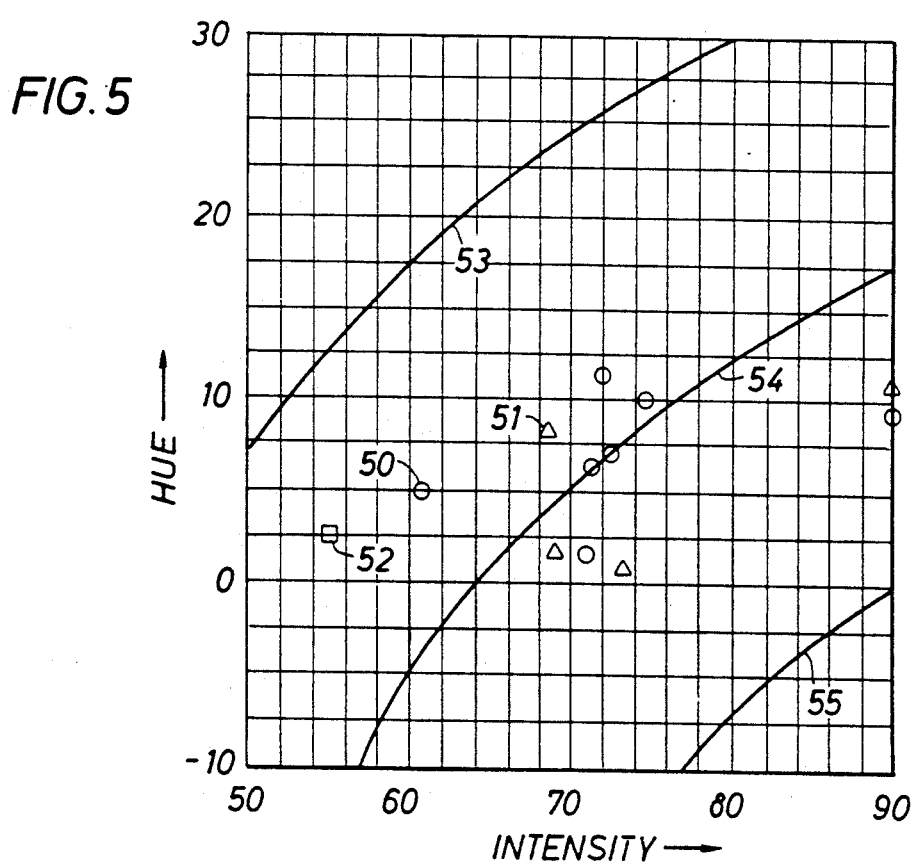

COLOR ANALYSIS OF ORGANIC CONSTITUENTS IN SEDIMENTARY ROCKS FOR THERMAL MATURITY

FIELD OF THE INVENTION

This invention relates generally to an analysis of the color of organic matter in a sample of sedimentary rock by which an accurate determination can be made of its present state of its thermal maturity. The present state of thermal maturity provides an indication of whether the sample has been heated sufficiently during past geological events to generate oil and/or natural gas in commercially interesting quantities.

BACKGROUND OF THE INVENTION

It is known to palynologists, organic petrologists and others that the thermal history of a sedimentary rock, often referred to as its organic metamorphism or eometamorphism, can be manifested in the color of the organic matter (commonly known as kerogen) that is extracted from a specimen or core sample of the rock. The color of the kerogen, when viewed in transmitted light, provides a type of paleothermometer. It has been recognized that the present state of thermal maturity of the kerogen is a useful indicator of whether it has been heated sufficiently by or during various historical geological events to generate oil and/or natural gas. If so, the kerogen is said to be thermally mature.

During increasing thermal maturity, palynomorphs such as spores, pollen, and plant tissue fragments undergo a variety of changes in color. These substances, when found in a sedimentary rock which is considered to be immature, vary in color from colorless or chartreuse to yellow; in mature sediments they vary in color from yellow-orange and orange-brown to a light brown; in over-mature sediments they vary in color from light brown to brown; in severely altered sediments they vary in color from brown to dark brown; and in sediments that have been metamorphosed they vary in color from dark brown to black.

Sediments that contain organic matter which have generated oil are those characterized above as being thermally mature. Over-mature sediments are likely to contain organics that are in the wet or dry gas phase of hydrocarbon generation, while those classified as severely altered contain organics which may produce dry gas, hydrogen sulfide and/or carbon dioxide. Thus, a precise determination of the color of the kerogen provides a useful indicator of whether oil might be found by drilling into a certain sedimentary layer of rocks, or whether the strata is thermally too young (cold) or old (hot) to warrant the high expenses involved in exploration drilling.

Kerogen materials such as spores, pollen, plant tissue and the like are known to exhibit a variety of colors, even within the same specimen or sample. Previous color analysis systems have relied solely upon visual estimates of spore coloration and have a disadvantage in that they are highly subjective. Because of this, it is extremely difficult to define a particular color, or to erect a color scheme, that is acceptable to everyone. Therefore, different analysts will come up with different thermal maturity estimates based upon the same sample. Another commonly used analytical system uses measurements of percentage vitrinite reflection to estimate thermal maturity. However, these measurements are limited to spot readings of small diameter areas of the specimen, and the system also involves a high degree of subjectivity, particularly where anisotrophy is present. Moreover, even experts have difficulty in picking out the vitrinite in a specimen. This technique also requires that a specimen slide be exactly levelled before a meaningful measurement of reflectivity can be made. Another system described in U.S. Pat. No. 4,971,437 issued Nov. 20, 1990, employs optical spectral analysis with rapid spectral scanning which measures the wavelength of light. Two light sources are used alternatively, one providing a beam of transmitted light that passes through the rock sample held in a plate, and another beam of incidental light that causes the sample to fluoresce. A filter disk is rotated through the light beam which filters the same through a range of wave lengths, and electrical signals are generated which are representative of the intensity of the light to provide a spectral output. This method required specially designed equipment and optical systems which are very expensive to manufacture and, since amorphous debris is the organic component being measured, the analyst does not know precisely what is being measured. Moreover, the method disclosed in the '437 patent does not provide an integrated approach, as does the present invention where measurements are made of an entire spore or pollen grain.

The present invention uses the concept that color is defined by three parameters: hue, saturation and brightness. Hue denotes the particular color which our eyes perceive, for example red, green or blue or various mixtures thereof. Saturation refers to the lack of "whiteness" in a color, or more precisely, how much a color differs from neutral. On the other hand brightness, also called intensity, is a parameter that describes the perceived brilliance of color (hue) of light. For example, the sun at noon appears to have a yellow hue which is strongly saturated and extremely brilliant. However, at sunset the hue shifts to a deep blood-red color, is more highly saturated, and is less brilliant. A certain combination of these three parameters corresponds to a distinctive wavelength of visible light. The use of all of these parameters in accordance with the present invention has been found to provide much more definitive analysis than one based upon an estimated color or a particular color scheme, and even allows an analysts who may suffer from a degree of color blindness to accurately define the color of an organic constituent extracted from a rock sample.

An object of the present invention is to provide a new and improved kerogen color analysis method that obviates the above-mentioned problems and disadvantages with prior art systems and methods.

Another object of the present invention is to provide a new and improved color analysis method which virtually eliminates subjectively on the part of the analyst.

Another object of the present invention is to provide a new and improved color analysis system that is not limited to spot readings, but is based upon overall or truly integrated measurements of color values.

Still another object of the present invention is to provide a color analysis system that relies on measurement and recording of hue, saturation and brightness values which are the coordinates used in universally accepted charts which define color.

SUMMARY OF THE INVENTION

These and other objects are obtained in accordance with the concepts of the present invention through practice of methods for determining the color of organic matter extracted from a rock sample, which include the steps of using a high power microscope and a high resolution color video camera to photograph a slide-mounted specimen under transmitted illumination, and connecting the output of the camera to a frame grabber board and processor in a programmed digital computer so that values representing the red, green, blue (RGB) and the hue, saturation and brightness (HSB) parameters mentioned above are acquired. After the system has been calibrated with a standard having a known color value, an image of the specimen is captured on a remote multi-sync monitor where the area to be examined, which can be a spore, for example, is outlined by a remote control. RGB components of the color are then measured. Machine computation is used to calculate corrected HSB values, which are converted to maximum temperature values and expressed as a level of thermal maturity so as to reflect the degree to which the kerogen in the sample has been heated. The results preferably are plotted in a histogram form, and can be made available for illustration for a single specimen, an entire sample, and/or an entire well profile.

BRIEF DESCRIPTION OF THE DRAWINGS

The present invention has other objects, features and advantages which will become more clearly apparent in connection with the following detailed description of a preferred embodiment, taken in conjunction with the appended drawings in which:

FIGS. 3A and 3B are schematic views which show the connections between the central processing unit, the camera and the monitor;

FIG. 5 is a histogram plot with a thermal maturity pathway and showing hue and intensity values that have been determined in accordance with the present invention.

DETAILED DESCRIPTION OF A PREFERRED EMBODIMENT

Figure 1:
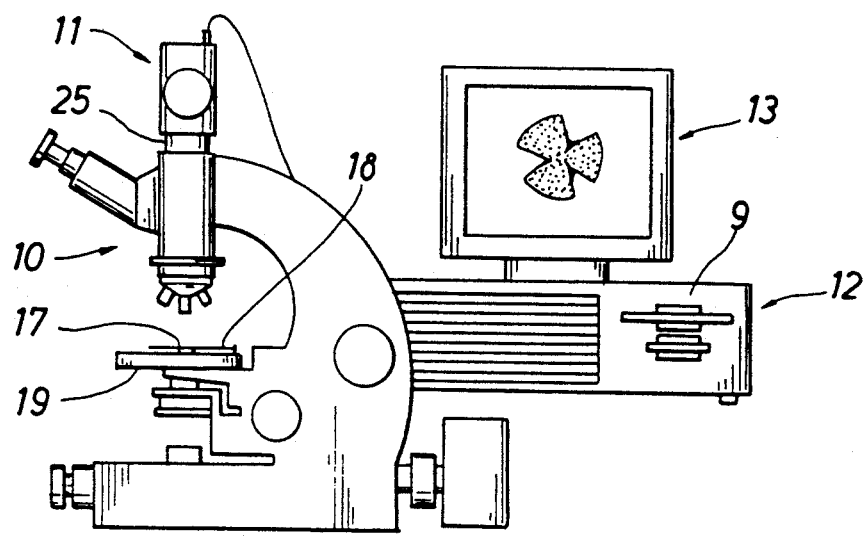
FIG. 1 is a schematic view showing various apparatus components by which the present invention is practiced.

Referring initially to FIG. 1, a color analysis method in accordance with this invention is carried out with the aid of a microscope 10, a color video camera 11, a computer 12 and a remote terminal monitor 13. The microscope 10 is readily available from manufacturers such as Jena, Leitz, Zeiss and others, and the camera 11 can be purchased from sources such as Javilin, Panasonic, Sony and others. The computer 12 can be any general purpose digital device, with either a 286 or 386 central processing unit 9 (CPU). The CPU 9 is equipped with a frame grabber/processor board 14 as shown in FIG. 3, which is a standard item available from American Innovisions, Jandel Scientific, American Telephone & Telegraph, and others. Of course a keyboard (not shown) is provided to enable commands to be given to the CPU 9 so that certain calculations and other functions can be performed under the control of a program.

Figure 2:
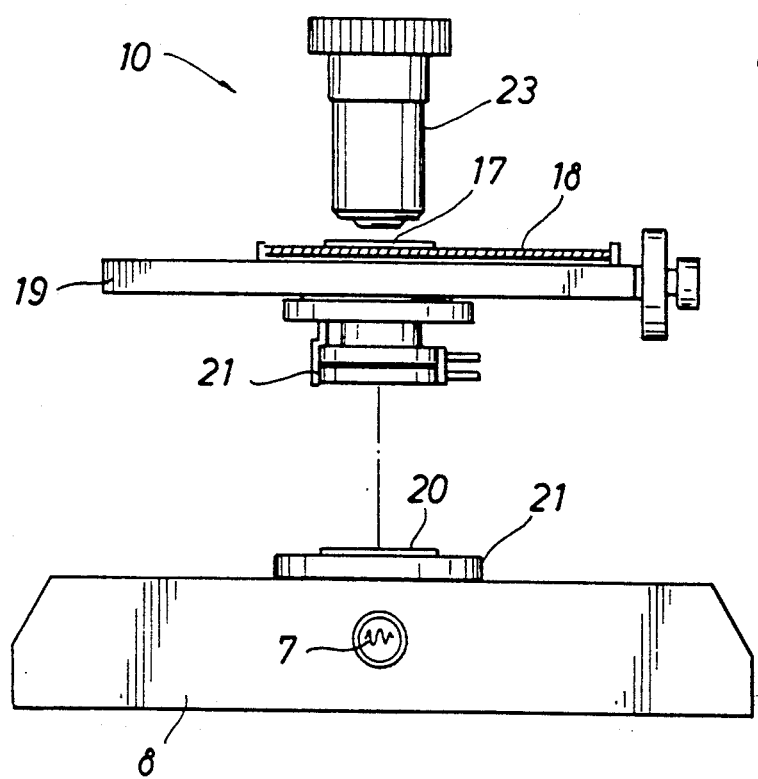
FIG. 2 is a front plan view of the microscope, slide and illumination set-up.

The input ports of the board 14 are electrically coupled to a connector 15 on top of the camera 11 by a cable 16 which conveys electrical signals representing the red, green and blue colors that are detected when light is transmitted through a specimen 17 which is mounted on a slide 18 on the stage 19 of the microscope 10. As shown in more detail in FIG. 2, the light source 7 for the microscope 10 is a quartz halogen bulb mounted in the base 8 of the microscope. A daylight correction filter 20 placed over the field diaphragm 21 converts the equivalent temperature of the light source 7 to about 3300° to 3500° K., which is the approximate color temperature of sunlight. The light coming out of the filter 20 passes through a sub-stage condenser (aperture) diaphragm 21, which can be used to adjust the RGB values to a standard that is used to calibrate the system. From there the light passes through the slide 18 and the specimen 17 which are mounted on the stage 19 of the microscope 10. The microscope 10 preferably has a 40X object lens assembly 23.

As shown in FIGS. 3A and 3B, the output ports of the frame grabber/processor board 14 are coupled to another cable 24 which is connected to the monitor 13. The monitor 13 is a multi-sync device for purposes of this invention. A collar on the bottom side of the camera 11 is connected to the top of the photo tube 25 of the microscope 10. The camera 11 has an electrical power socket 26 on its top side by which it is connected by a suitable electrical conductor cable to an outlet.

Figure 4:
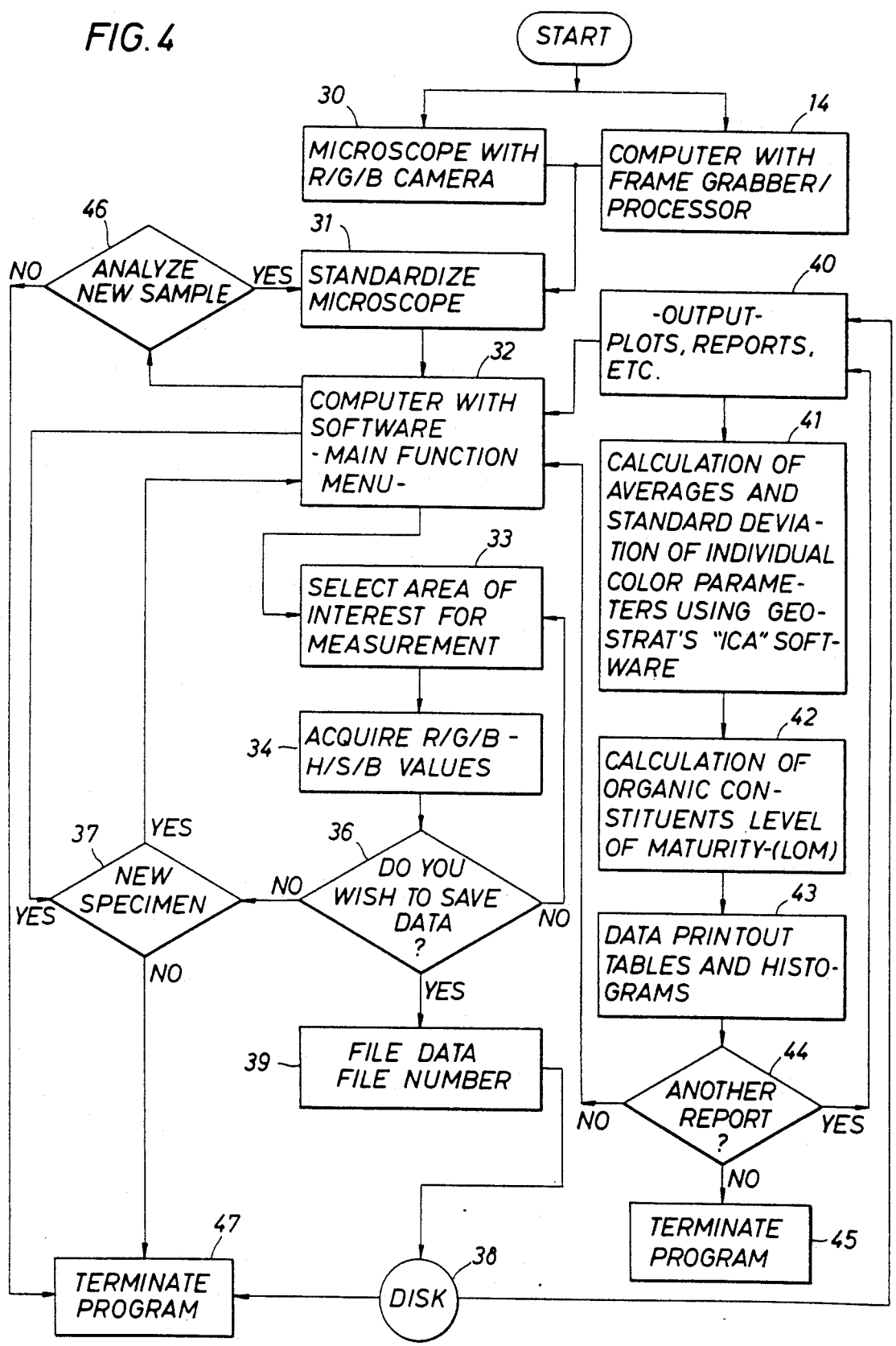
FIG. 4 is a block-type flow diagram showing the practice of the invention.

FIG. 4 illustrates in a simplified block diagram the analysis procedures which are carried out in accordance with the present invention, and how the computer 12, the processor board 14 and the microscope/camera combination 10, 11 coact with each other. Once the microscope/camera (block 30) has been standardized (block 31), the main function menu (block 32), which is the basic program, is used to provide a signal from the microscope/camera (block 30) to the computer 12 (block 32). The main program and function menu can utilize a program similar to that known as Image Pro which is available from Media Cybernetics Inc., Silver Spring, Md.

From this point the program proceeds to either re-standardize the microscopic 10 (block 31), or to select an area of interest of the specimen 17 which is to be analyzed (block 33). Once the image of the specimen 17 has been captured, it is displayed on the remote video display terminal 13. One example of organic matter that might be displayed is shown on the monitor screen in FIG. 1 is a pollen grain indicative of a flowering plant in the Miocene or Upper Cretaceous periods. The precise area of the image on the screen to be measured then is outlined by the analyst, for example by tracing the outline of the pollen grain by using a cursor/pointer, or with the aid of a "mouse". In accordance with an important feature of the present invention, measurements are made on a per-pixel basis, and the number of pixels within the outlined area is also displayed. For example, the number of pixels in the outline of a spore from a simple fern which grew early in the earth's history might be approximately 3,000. The RGB-HSB values for each pixel within the outlined area then are read by the microscope-camera combination (block 30) and the resulting signals are fed to the computer 12 (block 32), and are more precisely defined in block 34. The program then continues to a decision point where the analyst decides whether to save the data (block 36), cancel the entire operation, re-evaluate the same specimen, or go to a new specimen which will be measured (block 37). In the event the RGB-HSB data is saved, the program is instructed to go to a File Data/File Number (block 39). Once the RGB-HSB values are assigned a file number, the data is saved on a disk (block 38). Now the data can be either retrieved from the disk (block 38) into an output (block 40), from which the data can be used to make various calculations at blocks 41 and 42, and the results printed out or plotted by a printer/plotter (block 43) in a table and/or histogram form. A decision point (block 44) is decided as to whether another report is needed (block 40) or whether the analyst wants to return to the main menu (block 32). The entire program also can be terminated at this point (block 45). Provided the analyst returns to the main function menu (block 32), a decision is made to either select a new specimen (block 37), analyze a new specimen (block 46), or terminate the program (block 47).

Measurements of RGB-HSB values can be made on a single specimen having a known time-stratigraphic range, or on a plurality of such specimens. After calculation, the results preferably are plotted on a maturation histogram of the type shown in FIG. 5. Of course the results then can be edited and replotted, or left alone. Preferably the hue or H values are plotted along the vertical axis of the plot (ordinate), and the intensity (brightness) values are plotted along the horizontal axis (abscissa). Those points shown by circles 50, triangles 51, and squares 52 can be points from different slides, or from different points on the same slide. The curved lines 53-55 represent a portion of a thermal maturity pathway with the line 54 being its center. The regions between lines that radiate upward and to the left from a point at the −90, +250 crossing can be used on a plot like FIG. 5 to show late, middle and early thermal maturity. Points falling in the middle region typically indicate a thermal maturity appropriate for the generation of oil. The program is arranged to illustrate and define RGB and HSB values ranging from 1 to about 255, each of which can be subdivided into tenths. The drawing figure depicts intensity values ranging from 55 to 90, and hue values from 0 to 30. Preferably the hue values show a 90° rotation about the zero axis to account for both positive and negative values. However, the negative hue values normally are not used to define color.

Thus the analysis system of the present invention uses the measured HGB-HSB values to define the present state of thermal maturity of the organic constituents extracted from a sedimentary rock. The present state of thermal maturity indicates whether the kerogen in the sample has been heated sufficiently by or during past geological events to generate oil and/or gas. It now will be recognized that a new and improved color analysis method and apparatus has been disclosed which meets all the objectives of the present invention. Since certain changes or modifications may be made in the disclosed embodiment without departing from the inventive concepts involved, it is the aim of the appended claims to cover all such changes and modifications falling within the true spirit and scope of the present invention.

What is claimed is:

1. A method of defining the present state of thermal maturity of a specimen of organic matter extracted from a rock sample, comprising the steps of: mounting a specimen of said matter on the stage of a microscope; transmitting light through said specimen; photographing said specimen with a color video camera mounted on said microscope which provides output signals representative of red, green and blue, and the hue, saturation and brightness values of said specimen; and using said signals to compute the present state of thermal maturity of said specimen.

2. The method of claim 1 including the further step of plotting said values on a thermal maturation pathway histogram having hue values on its ordinate and intensity values on its abscissa.

3. The method of claim 1 including the further step of filtering said light before it passes through said specimen to obtain the approximate color of sunlight.

4. The method of claim 1 wherein each of said values is calculated on a per-pixel basis, and including the further step of integrating said values to determine said present state of thermal maturity.

5. Apparatus for use in determining the present state of thermal maturity of a specimen of organic matter extracted from a rock sample, comprising: a microscope having a base, a stage on which said specimen is mounted, and an object lens assembly for magnifying a view of said specimen; illuminating means in said base to allow viewing of said specimen in transmitted light; color video camera means mounted on said lens assembly and arranged to provide an image of said specimen, said camera means being adapted to provide output signals representative of the red, green, and blue and the hue, saturation and brightness values of said image; a remote terminal monitor means to allow viewing of said image and selection of a particular area of said image for analysis; and computer means for calculating present thermal maturity of said specimen based upon values obtained in said selected area.

6. The apparatus of claim 5 further including means for adjusting said color values with respect to a chromatic standard.

7. The apparatus of claim 5 further including means for filtering said transmitted light to adjust the wavelength thereof to a certain range.

8. The apparatus of claim 5 further including plotter means connected to said computer means for providing a display of said values in a histogram form that shows a thermal maturation pathway.

* * * * *